United States Patent [19]

Clingan et al.

[11] 4,440,954

[45] Apr. 3, 1984

[54] PROCESS FOR THE PURIFICATION OF P-AMINOPHENOL

[75] Inventors: William R. Clingan, Ferguson; Edward L. Derrenbacker, Creve Coeur; Thomas J. Dunn, Jefferson County, all of Mo.

[73] Assignee: Mallinckrodt, Inc., St. Louis, Mo.

[21] Appl. No.: 251,461

[22] Filed: Apr. 20, 1981

Related U.S. Application Data

[63] Continuation-in-part of Ser. No. 156,661, Jun. 5, 1980, abandoned.

[51] Int. Cl.$^3$ ............................................. C07C 89/04
[52] U.S. Cl. ................................................... 564/439
[58] Field of Search ......................... 564/439; 260/575

[56] References Cited

U.S. PATENT DOCUMENTS

| | | | |
|---|---|---|---|
| 3,383,416 | 5/1968 | Benner | 564/418 |
| 3,717,680 | 2/1973 | Baron et al. | 564/439 |
| 3,845,129 | 10/1974 | Reid | 564/439 |
| 3,876,703 | 4/1975 | Harmetz et al. | 564/439 |
| 4,139,562 | 2/1979 | Yomamoto et al. | 564/439 |
| 4,171,138 | 11/1979 | Sathe | 564/439 |

FOREIGN PATENT DOCUMENTS

451026  9/1948  Canada ............................. 564/439

*Primary Examiner*—Natalie Trousof
*Assistant Examiner*—Raymond Covington
*Attorney, Agent, or Firm*—Senniger, Powers, Leavitt and Roedel

[57] ABSTRACT

An improved process for the recovery and extractive purification of p-aminophenol is disclosed. The process involves contacting an aqueous feed solution prepared by catalytic reduction of nitrobenzene in acid medium and containing 4,4-diaminodiphenyl ether, aniline and other minor amine by-products with a base to adjust the pH of the solution to 4.0–5.0, and then extracting the resulting aqueous feed solution with a mixture of aniline and toluene to selectively dissolve 4,4'-diaminodiphenyl ether in the aniline-toluene mixture and to produce an aqueous phase containing principally p-aminophenol and an organic aniline-toluene phase cotaining p-aminophenol, 4,4'-diaminodiphenyl ether and other amine by-products. The ratio of aniline to toluene is within the range between approximately 4 parts by volume aniline to 1 part by volume toluene and approximately 1 part by volume aniline to 4 parts by volume toluene, preferably a ratio of 1:1. After separation of the aqueous phase from the organic phase, the p-aminophenol of improved purity is recovered from the aqueous phase. Further efficiency in the overall yield of p-aminophenol is achieved by back-extracting the organic phase with a basic solution of potassium or sodium hydroxide to produce an aqueous layer containing the basic solution and substantially all of the p-aminophenol formerly contained in the organic phase and then recycling the aqueous layer for use as a portion of the base used to adjust the pH of the original aqueous feed solution to the range of 4.0 to 5.0. Another feature disclosed is the fractional countercurrent extraction of the original aqueous feed solution having a pH of 4.0 to 5.0 with an aniline-toluene mixture and an ammonium sulfate solution, aniline sulfate or sulfuric acid to selectively dissolve 4,4'-di-aminodiphenyl ether in the aniline-toluene mixture and to produce an aqueous phase from which a greater yield of p-aminophenol of improved purity may be obtained.

33 Claims, No Drawings

PROCESS FOR THE PURIFICATION OF P-AMINOPHENOL

CROSS-REFERENCE TO RELATED APPLICATION

This application is a continuation-in-part of U.S. Pat. application Ser. No. 156,661, filed June 5, 1980 now abandoned.

BACKGROUND OF THE INVENTION

This invention relates to the purification of p-aminophenol and, more particularly, to a process for the recovery and extractive purification of p-aminophenol which more selectively removes the principal impurity of concern, namely, 4,4'-diaminodiphenyl ether.

p-Aminophenol (PAP) is a well known and important chemical intermediate used in the preparation of the analgesic, acetaminophen (APAP). It is also used as an intermediate in the production of dyestuffs and photographic chemicals. A high degree of purity, particularly with respect to 4,4'-diaminodiphenyl ether, is desirable for p-aminophenol especially as regards its use in the preparation of acetaminophen.

An important commercial and widely used method for the preparation of PAP involves the catalytic hydrogenation of nitrobenzene in a strongly acid medium. In the basic process, hydrogenation of nitrobenzene is carried out in the presence of a 10-13% sulfuric acid solution containing a small amount of a surfactant such as dodecyltrimethylammonium chloride, and employing a platinum-on-carbon catalyst. The reaction is somewhat complex and yields, in addition to the desired PAP, a significant amount of aniline as well as a number of minor amine by-products, including 4,4'-diaminodiphenyl ether (also known as oxydianiline or ODA), o-aminophenol, p-aminodiphenylamine and p-hydroxydiphenylamine. These by-products, which are potential impurities in the PAP end product, are generally soluble in the acidic aqueous media. 4,4'-Diaminodiphenyl ether is the principal minor amine byproduct and, for use of PAP in preparing pharmaceutical compounds, its presence therein should be less than 20 ppm and preferably less than 10 ppm.

In a particularly advantageous process for the preparation of PAP by the catalytic hydrogenation of nitrobenzene in aqueous sulfuric acid (see Benner U.S. Pat. application Ser. No. 3,383,416, dated May 14, 1968), the hydrogenation reaction is interrupted prior to the consumption of all the nitrobenzene charged into the reactor. The catalyst tends to suspend in the nitrobenzene layer, and the aqueous reaction mixture, containing the PAP, aniline and the minor amine byproducts in the form of salts, is readily separated by decantation.

As stated, PAP which is used in the preparation of APAP should preferably be quite pure, expecially with respect to 4,4'-diaminodiphenyl ether. A number of processes directed to improving the purification of p-aminophenol have been described in the patent literature. In addition to Benner U.S. Pat. Ser. No. 3,383,416, the following patents are pertinent to processes for preparing p-aminophenol:

U.S. Pat. No. 3,658,905
U.S. Pat. No. 3,694,508
U.S. Pat. No. 3,703,598
U.S. Pat. No. 3,717,680
U.S. Pat. No. 3,845,129
U.S. Pat. No. 3,876,703
U.S. Pat. No. 3,917,695
U.S. Pat. No. 4,139,562
U.S. Pat. No. 4,176,138
Brit. Pat. No. 1,028,078
Brit. Pat. No. 1,038,005
Brit. Pat. No. 1,228,568
Brit. Pat. No. 1,291,642
Brit. Pat. No. 1,516,380
Japanese Pat. No. SHO 54(1979)-73741

In Baron et al. U.S. Pat. Ser. No. 3,717,680, aniline is added to the aqueous reaction product from the basic Benner process and the pH is increased to a value above 6.0, preferably 6.5-7.5, at which the PAP is in the free amine form. The solution is then cooled and the PAP crystallizes out, is filtered off and washed, first with aniline and then with toluene. The aniline phase, containing 4,4'-diaminodiphenyl ether and other minor amine byproducts is then separated from the aqueous phase.

Japanese Pat. No. SHO 54(1979)-73741 discloses a process for producing purified p-aminophenol in which the catalytic reduction reaction mixture resulting from the catalytic reduction of nitrobenzene is partially neutralized with an alkali to a pH of 3.5 to 5. An aromatic amine such as aniline is then added and 4,4'-diaminodiphenyl ether and other impurities associated with sulfuric acid in the aqueous phase are selectively replaced with the aromatic amine. The liberated impurities are removed by extraction with excess aromatic amine. The aromatic amine phase recovered is washed with an aqueous alkali solution and recycled and used for the partial neutralization of the catalytic reduction reaction mixture.

Reid U.S. Pat. Ser. No. 3,845,129 discloses a process for the recovery of p-aminophenol in purified form prepared by catalytic reduction of nitrobenzene whereby aniline and 4,4'-diaminodiphenyl ether are present as impurities, the process involving contacting a solution of p-aminophenol and the impurities in an aqueous medium having a pH of 4.8 to 5.5, particularly 5.0 to 5.5, just short of that at which precipitation of p-aminophenol occurs and at which aniline and 4,4'-diaminodiphenyl ether are in the form of free bases with an extraction medium consisting essentially of a non-oxygenated solvent immiscible with water such as methylene dichloride, chloroform, carbon tetrachloride, etc. The solvent selectively dissolves the impurities and p-aminophenol of improved purity is recovered from the aqueous phase. Toluene is listed as being a relatively poor solvent for 4,4'-diaminodiphenyl ether.

Yamamoto U.S. Pat. Ser. No. 4,139,562 discloses a process for purifying crude p-aminophenol in which the latter obtained by catalytically reducing nitrobenzene in an aqeuous sulfuric acid medium is added with an alkali in an atmosphere of an inert gas, such as nitrogen, and in the presence of a reducing agent, such as sodium dithionite or sodium sulfite, to adjust the pH to 7-8 and the resulting precipitate of crude p-aminophenol is separated from the liquid phase. The separated p-aminophenol is then redissolved in an aqueous metal solution to form an aqueous solution of an alkali metal salt of crude p-aminophenol which is contacted with an inert organic solvent immiscible with water to permit the impurities present in the system to be selectively extracted in the organic solvent. The preferred organic solvent is aniline.

Sathe U.S. Pat. Ser. No. 4,176,138 discloses a method for preparing p-aminophenol by the catalytic hydrogenation of nitrobenzene in an acid reaction medium in which dimethyldodecylamine sulfate is substituted for trimethyldodecylammonium chloride to eliminate certain impurities.

Harmetz et al. U.S. Pat. Ser. No. 3,876,703 disclose a method of purifying crude p-aminophenol involving the preparation of a mixture of an aqueous solution of the crude p-aminophenol and nitrobenzene, adjusting the pH of the mixture to between 4.5 and 7.5 and separating a nitrobenzene phase.

While these purification schemes and others disclosed in the above-mentioned patent literature possess some degree of utility, a need continues to exist for a purification process which is more selective as to the removal of 4,4'-diaminodiphenyl ether from PAP, which provides PAP of improved purity in greater overall yields, and which avoids the losses of PAP inherent in the prior art processes.

SUMMARY OF THE INVENTION

Among the objects of the present invention may be mentioned the provision of an improved process for the recovery and extractive purification of p-aminophenol; the provision of such a process which produces p-aminophenol having a 4,4'-diaminodiphenyl ether content lower than 20 ppm or even less than 10 ppm; the provision of an improved process of the type mentioned in which greater purification of p-aminophenol is achieved with a smaller overall loss of p-aminophenol; the provision of such a process in which aniline-toluene mixtures are used to effect improved purification yields by maximizing the removal of 4,4'-diaminodiphenyl ether and minimizing the loss of p-aminophenol; the provision of such a process in which the overall yield of p-aminophenol of improved purity is achieved by recycling p-aminophenol not recovered from the first extraction step but obtained through a later back extraction step; and the provision of such a process which may be carried out utilizing conventional equipment. Other objects and features will be in part apparent and in part pointed out hereinafter.

Briefly, the present invention is directed to a process for the recovery and extractive purification of p-aminophenol prepared by catalytic reduction of nitrobenzene in acid medium whereby 4,4'-diaminodiphenyl ether and aniline are present as impurities which involves first neutralizing an aqueous feed solution containing p-aminophenol and the mentioned impurities with a base to adjust the pH of the solution to between approximately 4.0 and 5.0. The resulting aqueous feed solution is next extracted with a mixture of aniline and toluene to selectively extract 4,4'-diaminodiphenyl ether in the aniline-toluene mixture and to produce an aqueous phase containing principally p-aminophenol and an organic aniline-toluene phase containing p-aminophenol, 4,4'-diaminodiphenyl ether and other amine by-products. The aqueous phase is separated from the organic phase and p-aminophenol of improved purity is then recovered from the aqueous phase.

In another feature of the process of the invention whereby the overall yield of p-aminophenol of improved purity is achieved, the organic phase containing aniline, p-aminophenol and 4,4'-diaminodiphenyl ether, is back extracted by treatment with a basic solution of potassium or sodium hydroxide to produce an aqueous layer containing the basic solution and substantially all of the p-aminophenol formerly contained in the organic phase and a residual organic phase containing substantially all of the 4,4'-diaminodiphenyl ether formerly contained in the organic phase, and the aqueous layer is recycled and utilized as a portion of the base employed to adjust the pH of the original aqueous feed solution to between approximately 4.0 and 5.0.

In lieu of potassium or sodium hydroxide, the organic phase may be back extracted by treatment with a solution of ammonium sulfate which has had its pH adjusted to between approximately 4.8 and 5.0. In still another embodiment of the invention, the advantages of overall yield improvement and the production of p-aminophenol of greater purity may both be realized by a fractional countercurrent extraction of an aqueous feed solution containing p-aminophenol and the aforementioned impurities and having a pH between approximately 4.0 and 5.0 with an anilinetoluene mixture and an ammonium sulfate solution, aniline sulfate or sulfuric acid whereby 4,4'-diaminodiphenyl ether is selectively extracted into the aniline-toluene mixture and an aqueous phase containing principally p-aminophenol and an organic aniline-toluene phase containing p-aminophenol, 4,4'-diaminodiphenyl ether and other by-product amines are produced. The aqueous phase is then separated from the organic phase and p-aminophenol of improved purity is recovered from the aqueous phase as before.

DESCRIPTION OF THE PREFERRED EMBODIMENTS

In accordance with the present invention, it has now been found that p-aminophenol of improved purity may be prepared through a recovery and extractive purification process in which an aqueous feed solution, containing p-aminophenol, and aniline and 4,4'-diaminodiphenyl ether as impurities, obtained in a conventional manner from the catalytic reduction of nitrobenzene in acid medium, is first contacted with a base to adjust the pH of the feed solution to between approximately 4.0 and 5.0 and is then extracted with an organic solvent consisting of a mixture of aniline and toluene. It has been found that under these particular pH conditions and with such an organic solvent, the primary impurity of concern, namely, 4,4'-diaminodiphenyl ether, is more selectively extracted into the organic solvent phase making possible the preparation of p-aminophenol of improved purity, i.e. p-aminophenol containing less than 20 ppm of 4,4'-diaminodiphenyl ether and more desirably, as illustrated by the experimental examples set forth hereinafter, even less than 10 ppm of 4,4'-diaminodiphenyl ether.

As stated, the starting material for the process of the present invention is an aqueous feed solution containing p-aminophenol and aniline, 4,4'-diaminodiphenyl ether and other minor amine by-products which results from the catalytic reduction of nitrobenzene in sulfuric acid medium such as that described in Benner U.S. Pat. Ser. No. 3,383,416. The aqueous feed solution may also contain a small proportion of unreacted nitrobenzene or it may be treated to remove substantially all of the nitrobenzene prior to initiating the practice of the present invention.

The aqueous feed solution is first contacted with a base to adjust the pH of the solution to approximately 4.0–5.0. This is an important feature of the invention since at this pH range, 4,4'-diaminodiphenyl ether, aniline and the minor amine by-products, being weaker bases than p-aminophenol, will be liberated in the free amine form while p-aminophenol remains principally in the form of its sulfate salt. Thus, the difference in basicities of these compounds permits the undesired components to be present in free amine form with the desired component being present as the sulfate salt of p-aminophenol.

As will be seen from the experimental results set forth hereinafter, a pH within the range 4.0 to 4.5 is more beneficial for retention of p-aminophenol in the aqueous phase while a pH within the range of 4.5 to 5.0 is more beneficial for the removal of 4,4'-diaminodiphenyl ether. However, within the scope of the present invention, both of these objectives can be met over the entire range of 4.0 to 5.0 by utilizing a sufficient number of extraction stages.

To achieve this pH adjustment of the aqueous feed solution to 4.0–5.0, the use of a base such as ammonia (which term includes ammonium hydroxide) or potassium hydroxide is highly preferred. However, any alkali metal hydroxide or alkali metal salt of p-aminophenol may also be used for this purpose. Further, a base solution containing potassium or sodium hydroxide and p-aminophenol resulting from the back extraction step described hereinafter may be recycled and utilized as a portion of the base used to achieve the pH adjustment of the aqueous feed solution to 4.0–5.0.

After the desired pH adjustment has been made, the aqueous feed solution is then extracted with a mixture of aniline and toluene to selectively dissolve the 4,4'-diaminodiphenyl ether and produce an aqueous phase or raffinate containing principally p-aminophenol and an organic aniline-toluene phase containing p-aminophenol, substantially all of the 4,4'-diaminodiphenyl ether formerly present in the aqueous feed solution, and other anilinetoluene soluble impurities. In accordance with the invention, we have found that the desired results are achieved when the ratio of aniline to toluene is within the range between approximately 4 parts by volume aniline to 1 part by volume toluene and approximately 1 part by volume aniline to 4 parts by volume toluene. Preferably, a ratio of 1 part by volume aniline to 1 part by volume toluene is employed for reducing PAP solubility losses in the organic solvent phase while providing equivalent removal of 4,4'-diaminodiphenyl ether. In such organic solvent mixtures, aniline functions as the extractant while toluene functions as an antisolvent and diluent. Thus, while toluene is essentially a poor solvent for p-aminophenol and 4,4'-diaminodiphenyl ether, we have found that when it is combined with aniline in the ratios set forth above, the resulting mixtures exhibit the desired solvent properties for the system as well as the desired physical properties.

The extraction of 4,4'-diaminodiphenyl ether from the aqueous feed solution as described may be carried out on either a batch or continuous basis. Perferably, the extraction is carried out in a countercurrent extraction column such as Karr reciprocating plate countercurrent extraction column or other similar columns known to those skilled in the art. Equipment such as a centrifugal countercurrent extractor, pumper-decanter, pulsed column or a mixer-settler apparatus may also be employed. Thus, using a Karr countercurrent extraction column for example, we have found that the 4,4'-diaminodiphenyl content of the aqueous p-aminophenol phase may be reduced to below 50 ppm and usually below 10 ppm with 3-4 theoretical extraction stages with a 50%–50% aniline-toluene mixture at a pH of 4.8 whereas it requires on the order of five stages with straight aniline and on the order of 16–20 cross-current extractions with straight aniline on a batch basis to achieve the same low 4,4'-diaminodiphenyl ether content at a constant organic to aqueous ratio.

We have also found that the volume ratio of aniline-toluene to aqueous feed solution is an important factor in the performance of the extraction step. In general, lower ratios are preferred since less p-aminophenol is extracted into the organic phase and consequently more p-aminophenlol will be found in the aqueous phase. Overall, volume ratios of aniline-toluene to aqueous feed solution of 0.05 to 1:1 may be employed with a ratio of 0.2:1 being preferred.

Once the extraction is completed, the aqueous phase or raffinate containing most of the p-aminophenol together with some aniline and a very minor amount (less than 50 ppm based on the p-aminophenol) of 4,4'-diaminodiphenyl ether is separated from the organic phase. The aqueous raffinate phase is then neutralized to a pH of 7–8, as by the addition of ammonium hydroxide, to precipitate the partially purified p-aminophenol product. Precipitation of p-aminophenol occurs between a pH of 5 to 8 but since the minimum solubility of p-aminophenol is between pH 7 and 8, most of the product is precipitated in this range.

The precipitated p-aminophenol is then collected by filtration and washed with toluene and a sodium bisulfite solution, and vacuum dried. The toluene removes any adhering aniline and the sodium bisulfite functions as an antioxidant. The dried p-aminophenol product, so obtained, typically contains less than 10 ppm of 4,4'-diaminodiphenyl ether and is of acceptable purity for use in preparing acetaminophen.

The organic phase or extract from the extraction step containing aniline, p-aminophenol and 4,4'-diaminodiphenyl ether may be subjected to distillation to recover the aniline for reuse or preferably may be subjected to further treatment as described below for recovery of additional p-aminophenol to improve the overall yield thereof.

Thus, preferably, the organic phase is subjected to back extraction by the addition thereto of a potassium or sodium hydroxide solution, preferably potassium hydroxide, whereby there is produced an aqueous layer containing the potassium or sodium hydroxide and substantially all of the p-aminophenol formerly contained in the organic phase and a residual organic phase containing substantially all of the 4,4'-diaminodiphenyl ether formerly contained in the organic phase. The concentration of the potassium or sodium hydroxide solution should be in excess of that required to convert the p-aminophenol to its phenolate salt form. In general, a concentration of 10–50% by weight of potassium hydroxide, for example, should be employed.

The pH of the aqueous layer obtained from the back extraction is in excess of 12. The pH of this aqueous layer may be adjusted to 7–8, as by the addition of concentrated sulfuric acid, to precipitate solids containing a technical grade of p-aminophenol. However, in accordance with the invention, it is highly preferred that the aqueous layer be recycled and used as a portion of the base employed to adjust the pH of the original aqueous feed solution to 4.0–5.0 and thereby reintroduce the unrecovered p-aminophenol from the aqueous layer into the main process stream to achieve a greater overall yield of p-aminophenol of improved purity through the basic extraction process previously described.

Aniline and toluene may be recovered from the residual organic phase by distillation and reused.

In lieu of back extracting the organic phase from the basic extraction step with a solution of potassium or sodium hydroxide, the organic phase may also be back extracted with an ammonium sulfate solution to achieve a greater overall yield of p-aminophenol.

Preferably, however, and in accordance with another feature of the invention, we have found that a greater yield of p-aminophenol of improved purity may be realized by fractionally extracting, in a countercurrent fashion, as in a Karr reciprocating plate extraction column, an aqueous feed solution containing p-aminophenol, aniline, 4,4'-diaminodiphenyl ether and other minor amine by-products and having a pH of 4.0 to 5.0 with a mixture of aniline and toluene and an ammonium sulfate solution of pH 4.0 to 5.0, aniline sulfate or sulfuric acid. For example a 15% ammonium sulfate solution having a pH of 4.8 to 5.0 or a 1.5% ammonium sulfate solution having a pH of 4.0 may be used for this purpose. In lieu of ammonium sulfate, either aniline sulfate or sulfuric acid may be used. When the latter is employed, it forms aniline sulfate with aniline present in the organic phase. The 4,4'-diaminodiphenyl ether is again selectively extracted into the aniline-toluene mixture. The extraction produces an aqueous phase which contains more of the p-aminophenol originally present in the aqueous feed solution than in the previously described extraction step in which the aniline-toluene mixtures were used without an ammonium sulfate solution for back extraction of p-aminophenol. The organic phase produced likewise contains substantially all of the 4,4'-diaminodiphenyl ether previously contained in the aqueous feed solution. The aqueous phase containing the p-aminophenol is separated from the organic phase and treated as before to obtain p-aminophenol of improved purity containing less than 10 ppm of 4,4'-diaminodiphenyl ether. The organic phase is available for aniline-toluene recovery and for further p-aminophenol recovery as previously described.

The following working examples further illustrate the practice of the invention.

EXAMPLE 1 p-Aminophenol hydrogenation liquors (10 l.) obtained by the catalytic hydrogenation of nitrobenzene in the presence of a platinum on carbon catalyst, 10–13% aqueous sulfuric acid and a minor amount of dodecyltrimethylammonium chloride (as described in R.G. Benner U.S. Pat. Ser. No. 3,383,416, dated May 14, 1968) were added to a 12 l. round bottom flask and the pH adjusted to 4.8–5.0 by the addition of concentrated ammonium hydroxide (1 l.). Alternatively, at this point, the aqueous phase containing potassium hydroxide and p-aminophenol (obtained as described in Example 2) may be utilized instead of a portion of the concentrated ammonium hydroxide. The aqueous p-aminophenol feed solution with its pH thus adjusted to 4.8–5.0 nominally contains, as their sulfate salts, 100 mg./ml. of p-aminophenol, 20 mg./ml. of aniline and 3 mg./ml. of 4,4'-diaminodiphenyl ether as the major constituents. The solution was heated to 85°–90° C. using a heating mantle and fed, via a heat insulated metering pump, to the top section of a Karr reciprocating plate extraction column with a plate stack 1" in diameter and 8' in height at approximately 250 ml./min. Simultaneously, a 50%—50% (by volume) mixture of aniline and toluene (about 1 l.) at a temperature of 85° C. was fed via a similar metering pump to the bottom section of the column at 50 ml./ min., so that the desired countercurrent flow pattern of droplet dispersion and coalescence was established in accordance with the normal operation of the extraction column. After equilibrium was achieved, the aqueous raffinate phase contained approximately 90 mg./ml. of p-aminophenol, 35 mg./ml. of aniline and less than 0.001 mg./ml. of 4,4'-diaminodiphenyl ether. The organic or aniline-toluene extract phase contained approximately 50 mg./ml. of p-aminophenol, 15 mg./ml of 4,4'-diaminodiphenyl ether and other aniline-toluene soluble impurities. The aqueous raffinate phase (11 l.) was collected and further neutralized with concentrated ammonium hydroxide to a pH of 7.0–8.0 to precipitate the partially purified p-aminophenol product. The product was collected by filtration, washed with toluene (750 ml.) and a 10% sodium bisulfate solution (300 ml.), and then vacuum dried. Approximately 950 grams of dry p-aminophenol containing less than 10 ppm of 4,4'-diaminodiphenyl ether was obtained. The organic extract was available for aniline recovery by distillation or for p-aminophenol recovery as described in Example 2 below.

EXAMPLE 2

Example 1 was repeated with the resulting hot organic extract phase (approx. 2.2 l.) being isolated and placed in a 5 liter round bottom flask equipped with an agitator. The organic phase was allowed to cool to ambient temperature. To the organic extract solution was added an aqueous potassium hydroxide solution (900 ml., 10% by weight) and the heterogeneous mixture was stirred for 15 minutes and allowed to settle for 5 minutes. The layers were then separated by decantation. The aqueous layer now contained approximately 97% of the p-aminophenol previously contained in the organic phase and approximately 1.5% of the 4,4'-diaminodiphenyl ether. The residual organic phase contained about 3% of the p-aminophenol and 98% of the 4,4'-diaminophenyl ether. The aqueous phase may be utilized in combination with ammonia or other base in the earlier neutralization step (adjusting pH of aqueous feed to pH 4.0–5.0) as described in Example 1 or processed separately for recovery of p-aminophenol. Addition of concentrated sulfuric acid to the aqueous phase (about 900 ml.) with cooling precipitated solids containing about 154 grams of technical p-aminophenol.

EXAMPLE 3

Example 1 was repeated with the exception that the pH of the aqueous feed was adjusted to 4.5 by the addition of concentrated ammonium hydroxide. After equilibrium was achieved, the resulting aqueous raffinate phase contained 97 mg./ml. of p-aminophenol, 35 mg./ml. of aniline and less than 0.001 mg./ml. of 4,4'-diaminodiphenyl ether. The organic extract phase contained approximately 16 mg./ml. of p-aminophenol and 15 mg./ml. of 4,4'-diaminodiphenyl ether in addition to other minor impurities.

EXAMPLE 4

Example 1 was repeated with the exception that the pH of the aqueous feed was adjusted to 4.0 by the addition of concentrated ammonium hydroxide. After equilibrium was achieved, the resulting aqueous raffinate phase contained 98 mg./ml. of p-aminophenol 35 mg./ml. of aniline and less than 0.001 mg./ml. of 4,4'- diaminodiphenyl ether. The organic extract phase contained approximately 12 mg./ml. of p-aminophenol and 15 mg./ml. of 4,4'-diaminodiphenyl ether in addition to other minor impurities.

EXAMPLE 5

Example 1 was repeated with the exception that the organic solvent feed was a 25%–75% (by volume) mixture of aniline and toluene. After equilibrium was achieved, the resulting aqueous raffinate phase contained 94 mg./ml. of p-aminophenol, 35 mg./ml. of aniline and 0.015 mg./ml. of 4,4'-diaminodiphenyl ether. The organic extract phase contained approximately 30 mg./ml. of p-aminophenol and 15 mg./ml. of 4,4'-diaminodiphenyl ether.

EXAMPLE 6

Example 1 was repeated with the exception that the organic solvent feed was a 75%–25% (by volume) mixture of aniline and toluene. After equilibrium was achieved, the resulting aqueous raffinate phase contained 88 mg./ml. of p-aminophenol, 35 mg./ml. of aniline and less than 0.001 mg./ml. of 4,4'-diaminodiphenyl ether. The organic extract phase contained 60 mg./ml. of p-aminophenol and 15 mg./ml. of 4,4'-diaminodiphenyl ether.

EXAMPLE 7

Example 1 was repeated with the p-aminophenol hydrogenation liquors and aniline-toluene being prepared for the Karr countercurrent extraction column in the same way, the pH of the p-aminophenol hydrogenation liquors being adjusted to 4.8–5.0 in the same way. Also prepared was 1 liter of a 1.5% ammonium sulfate solution having its pH adjusted to 4.0 by the addition of sulfuric acid. The p-aminophenol hydrogenation liquors, at 85° C., were center fed to the Karr column at 250 ml./min. The aniline-toluene and ammonium sulfate feeds were fed at 50 ml./min. and 85° C. to the bottom and top of the column, respectively. Column operation was conducted to provide 4 theoretical stages in the bottom half of the column and clean phase separations. After equilibrium was reached, the aqueous raffinate phase contained approximately 99 mg./ml. of p-aminophenol, 35 mg./ml. of aniline and less than 0.001 mg./ml. of 4,4'-diaminodiphenyl ether. The organic extract phase contained approximately 5 mg./ml. of p-aminophenol, 15 mg./ml. of 4,4'-diaminodiphenyl ether and other aniline-toluene soluble impurities. The aqueous raffinate (12 liters) was collected and treated as in Example 1. Approximately 990 grams of dry p-aminophenol containing less than 10 ppm of 4,4'-diaminodiphenyl ether was isolated.

EXAMPLE 8

Example 7 was repeated with the exception that an aniline sulfate solution prepared by titrating 2% sulfuric acid with aniline to a pH of 3.8 was used in lieu of the 1.5% ammonium sulfate solution. After equilibrium was reached, the aqueous raffinate phase contained 99.9 mg./ml. of p-aminophenol, 45 mg./ml. of aniline and less than 0.001 mg./ml. of 4,4'-diaminodiphenyl ether. The organic extract phase contained approximately 2 mg./ml. of p-aminophenol, 15 mg./ml. of 4,4-diaminodiphenyl ether and other minor impurities.

The results are summarized in the following table:

| EXAMPLE | ORGANIC AQUEOUS | ANILINE TOLUENE | pH | $(PAP)_{AQ}$ | $(\Phi\text{-}NH_2)_{AQ}$ | $(ODA)_{AQ}$ | $(PAP)_{ORG}$ | $(ODA)_{ORG}$ | PURIFICATION YIELD |
|---|---|---|---|---|---|---|---|---|---|
| 1 | .2/1 | 50/50 | 4.9–5.0 | 90 | 35 | <.001 | 50 | 15 | 90% |
| 3 | .2/1 | 50/50 | 4.5 | 97 | 45 | <.001 | 16 | 15 | 97% |
| 4 | .2/1 | 50/50 | 4.0 | 98 | 60 | <.001 | 12 | 15 | 98% |
| 5 | .2/1 | 25/75 | 4.9–5.0 | 94 | 35 | 0.015 | 30 | 15 | 94% |
| 6 | .2/1 | 75/25 | 4.9–5.0 | 88 | 35 | <.001 | 60 | 15 | 88% |
| 7 | .2/1.1 | 50/50 | 4.8–5.0 | 99 | 35 | <.001 | 5 | 15 | 99% |
| 8 | .2/1.1 | 50/50 | 4.5 | 99.9 | 45 | <.001 | 2 | 15 | 99.9% |

FOR FEED CONTAINING (PAP) ≃ 100 MG/ML, ($\Phi$-NH$_2$) ≃ 20 MG/ML, (ODA) ≃ 3 MG/ML

In view of the above, it will be seen that the several objects of the invention are achieved and other advantageous results attained.

As various changes could be made in the above methods without departing from the scope of the invention, it is intended that all matter contained in the above description shall be interpreted as illustrative and not in a limiting sense.

What is claimed is:

1. A process for the recovery and extractive purification of p-aminophenol prepared by catalytic reduction of nitrobenzene in acid medium whereby 4,4'-diaminodiphenyl ether and aniline are present as impurities, the process comprising neutralizing an aqueous feed solution containing p-aminophenol and said impurities with a base to adjust the pH of said solution to between approximately 4.0 and 5.0, extracting the resulting aqueous feed solution with an organic solvent consisting of mixtures of aniline and toluene within the range between approximately 4 parts by volume aniline to 1 part by volume toluene and approximately 1 part by volume aniline to 4 parts by volume toluene whereby 4,4'-diaminodiphenyl ether is selectively extracted into said organic solvent and an aqueous phase containing principally p-aminophenol and an organic anilinetoluene phase containing p-aminophenol, 4,4'-diaminodiphenyl ether and other minor amine by-products are produced, separating said aqueous phase from said organic phase and thereafter recovering p-aminophenol of improved purity from said aqueous phase.

2. A process as set forth in claim 1 wherein said base is selected from the group consisting of ammonia, an alkali metal hydroxide, an alkali metal salt of p-aminophenol and a mixture of ammonia and a potassium or sodium salt of p-aminophenol.

3. A process as set forth in claim 2 wherein said base is ammonia.

4. A process as set forth in claim 1 wherein the pH of said aqueous feed solution is approximately 4.0.

5. A process as set forth in claim 1 wherein said organic solvent consists of 50% by volume of aniline and 50% by volume of toluene.

6. A process as set forth in claim 2 wherein said base is a mixture of ammonia and a solution of potassium hydroxide containing p-aminophenol.

7. A process as set forth in claim 1 wherein p-aminophenol of improved purity is recovered from said aqueous phase by adjusting the pH of the aqueous phase to between approximately 7.0 to 8.0 to precipitate p-aminophenol.

8. A process as set forth in claim 1 wherein the volume ratio between the organic solvent and the aqueous feed solution ranges between approximately 0.05:1 and 1:1.

9. A process as set forth in claim 8 wherein said volume ratio is approximately 0.2:1.

10. A process as set forth in claim 1 wherein the extraction with said organic solvent is carried out in countercurrent fashion utilizing approximately 5 theoretical extraction stages.

11. A process as set forth in claim 7 wherein said recovered p-aminophenol is further washed with toluene and a sodium bisulfite solution, and dried.

12. A process as set forth in claim 1 wherein aniline is recovered from said organic phase by distillation.

13. A process as set forth in claim 1 wherein said organic phase is treated with a base consisting of a solution of potassium or sodium hydroxide to produce an aqueous layer containing said base and substantially all of the p-aminophenol formerly contained in the organic phase and a residual organic phase containing substantially all of the 4,4'-diaminodiphenyl ether formerly contained in the organic phase.

14. A process as set forth in claim 13 wherein said organic phase is treated with a base consisting of a solution containing approximately 10 to 50% by weight of potassium hydroxide.

15. A process as set forth in claim 1 wherein said organic phase is treated with an agent selected from the group consisting of an aqueous ammonium sulfate solution, aniline sulfate and sulfuric acid to produce an aqueous layer containing said agent and substantially all of the p-aminophenol formerly contained in the organic phase and a residual organic phase containing substantially all of the 4,4'-diaminodiphenyl ether formerly contained in the organic phase.

16. A process as set forth in claim 15 wherein said agent is a 15% aqueous ammonium sulfate solution having a pH between approximately 4.8 and 5.0.

17. A process as set forth in claim 15 wherein said agent is a 1.5% aqueous ammonium sulfate solution having a pH of approximately 4.0.

18. A process for the recovery and extractive purification of p-aminophenol prepared by catalytic reduction of nitrobenzene in acid medium whereby 4,4'-diaminodiphenyl ether and aniline are present as impurities, the process comprising contacting an aqueous feed solution containing p-aminophenol and said impurities with a base to adjust the pH of said solution to between approximately 4.0 and 5.0, extracting the resulting aqueous feed solution with an organic solvent consisting of mixtures of aniline and toluene within the range between approximately 4 parts by volume aniline to 1 part by volume toluene and approximately 1 part by volume aniline to 4 parts by volume toluene whereby 4,4'-diaminodiphenyl ether is selectively extracted into said organic solvent and an aqueous phase containing principally p-aminophenol and an organic aniline-toluene phase containing p-aminophenol, 4,4'-diaminodiphenyl ether and other minor amine by-products are produced, separating said aqueous phase from said organic phase, recovering p-aminophenol of improved purity from said aqueous phase, and treating said organic phase with a base consisting of a solution of potassium or sodium hydroxide to produce an aqueous layer containing said base and substantially all of the p-aminophenol formerly contained in the organic phase and a residual organic phase containing substantially all of the 4,4'-diaminodiphenyl ether formerly contained in the organic phase.

19. A process as set forth in claim 18 wherein said aqueous layer is recycled and utilized as a portion of the base employed to adjust the pH of the original aqueous feed solution to between approximately 4.0 and 5.0.

20. A process as set forth in claim 18 wherein the base for treating said organic phase is a solution containing approximately 10 to 50% by weight of potassium hydroxide.

21. A process as set forth in claim 18 wherein said organic solvent consists of 50% by volume of aniline and 50% by volume of toluene.

22. A process as set forth in claim 18 wherein p-aminophenol is recovered by adjusting said aqueous phase from the pH of the aqueous phase to between approximately 7.0 and 8.0 to precipitate p-aminophenol.

23. A process as set forth in claim 18 wherein the volume ratio between the organic solvent and the aqueous feed solution ranges between approximately 0.05:1 and 1:1.

24. A process as set forth in claim 23 wherein said volume ratio is approximately 0.2:1.

25. A process as set forth in claim 18 wherein the extraction with said organic solvent is carried out in countercurrent fashion utilizing approximately 5 theoretical extraction stages.

26. A process for the recovery and extractive purification of p-aminophenol prepared by catalytic reduction of nitrobenzene in acid medium whereby 4,4'-diaminodiphenyl ether and aniline are present as impurities, the process comprising fractional countercurrent extraction of an aqueous feed solution containing p-aminophenol and said impurities and having a pH between approximately 4.0 and 5.0 with an organic solvent consisting of mixtures of aniline and toluene within the range between approximately 4 parts by volume aniline to 1 part by volume toluene and approximately 1 part by volume aniline to 4 parts by volume toluene and an agent selected from the group consisting of an ammonium sulfate solution, aniline sulfate and sulfuric acid whereby 4,4'-diaminodiphenyl ether is selectively extracted into said organic solvent and an aqueous phase containing principally p-aminophenol and an organic aniline-toluene phase containing p-aminophenol, 4,4'-diaminodiphenyl ether and other minor amine by-products are produced, separating said aqueous phase and thereafter recovering p-aminophenol of improved purity from said aqueous phase.

27. A process as set forth in claim 26 wherein said agent is a 15% aqueous ammonium sulfate solution having a pH between approximately 4.8 and 5.0.

28. A process as set forth in claim 26 wherein said agent is a 1.5% aqueous ammonium sulfate solution having a pH of approximately 4.0.

29. A process as set forth in claim 26 wherein said organic solvent consists of 50% by volume of aniline and 50% by volume of toluene.

30. A process as set forth in claim 26 wherein p-aminophenol of improved purity is recovered from said aqueous phase by adjusting the pH of the aqueous phase to between approximately 7.0 and 8.0 to precipitate p-aminophenol.

31. A process as set forth in claim 26 wherein the volume ratio between the organic solvent and the aqueous feed solution ranges between approximately 0.05:1 and 1:1.

32. A process as set forth in claim 31 wherein said volume ratio is approximately 0.2:1.

33. A process as set forth in claim 26 wherein the extraction with said organic solvent and ammonium sulfate solution is carried out in countercurrent fashion utilizing approximately 5 theoretical extraction stages.

* * * * *